United States Patent
Wang et al.

(10) Patent No.: US 11,452,562 B2
(45) Date of Patent: Sep. 27, 2022

(54) DUAL COOLED RADIOFREQUENCY ABLATION PROBES TETHERED TOGETHER BY ELECTRICAL AND FLUID CONDUITS

(71) Applicant: Avent, Inc., Alpharetta, GA (US)

(72) Inventors: Ruoya Wang, Decatur, GA (US); Craig F. Steinman, Cumming, GA (US); Timothy J. Habegger, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 437 days.

(21) Appl. No.: 16/229,114

(22) Filed: Dec. 21, 2018

(65) Prior Publication Data

US 2020/0197085 A1 Jun. 25, 2020

(51) Int. Cl.
*A61B 18/14* (2006.01)
*A61B 18/18* (2006.01)
*A61B 18/00* (2006.01)

(52) U.S. Cl.
CPC ........ *A61B 18/1492* (2013.01); *A61B 18/148* (2013.01); *A61B 18/18* (2013.01); *A61B 2018/0016* (2013.01); *A61B 2018/00023* (2013.01); *A61B 2018/00577* (2013.01)

(58) Field of Classification Search
CPC ............... A61B 18/1492; A61B 18/18; A61B 2018/00023; A61B 2018/00089; A61B 2018/00577; A61B 2560/04; A61B 18/148; A61B 2018/00172; A61B 2018/00339; A61B 2018/0016
USPC ....................................................... 606/41
See application file for complete search history.

(56) References Cited

U.S. PATENT DOCUMENTS

| 9,956,032 | B1 | 5/2018 | Cosman et al. |
| 2005/0177209 | A1 | 8/2005 | Leung et al. |
| 2015/0320479 | A1* | 11/2015 | Cosman, Jr. ........... A61B 18/16 606/35 |

FOREIGN PATENT DOCUMENTS

| EP | 1 600 113 A2 | 11/2005 |
| EP | 2 942 023 A2 | 11/2015 |
| WO | WO 94/26186 A1 | 11/1994 |
| WO | WO 99/35983 A1 | 7/1999 |
| WO | WO 02/28475 A1 | 4/2002 |

(Continued)

OTHER PUBLICATIONS

International Search Report and Written Opinion for PCT/US2019/066687, dated Mar. 31, 2020, 11 pages.

*Primary Examiner* — Michael F Peffley
*Assistant Examiner* — Samantha M Good
(74) *Attorney, Agent, or Firm* — Meunier Carlin & Curfman LLC

(57) ABSTRACT

A dual cooled radiofrequency ablation probe assembly optimized for treatment of a patient's knee joint includes at least two cooled radiofrequency ablation probes. Each cooled radiofrequency ablation probe includes an electrically and thermally-conductive energy delivery device for delivering electrical or radiofrequency treatment to the patient. The probe assembly further includes cooling fluid tubing for supplying the at least two cooled radiofrequency ablation probes with cooling fluid, and an electrical cable for supplying the at least two cooled radiofrequency ablation probes with electrical energy. The at least two probes are tethered together by the cooling fluid tubing and the electrical cable.

19 Claims, 4 Drawing Sheets

(56) References Cited

FOREIGN PATENT DOCUMENTS

WO  WO 2013/016588 A1  1/2013

\* cited by examiner

DUAL COOLED RADIOFREQUENCY ABLATION PROBES TETHERED TOGETHER BY ELECTRICAL AND FLUID CONDUITS

FIELD OF THE INVENTION

The present invention relates generally to a system for applying energy for the treatment of tissue, and more particularly to a cooled radiofrequency ablation probe assembly that is optimized for treating a patient's knee.

BACKGROUND

Chronic joint pain, including osteoarthritis of the knee, is a major health problem resulting not only in debilitating conditions for the patient, but also in the consumption of a large proportion of funds allocated for health care, social assistance and disability programs. In joints, osteoarthritis is the most common form of arthritis pain and occurs when the protective cartilage on the ends of bones wears down over time. Currently, there are an estimated 30 million patients with osteoarthritis of the knee, with 10 million of those patients suffering from advanced symptoms of osteoarthritis.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The RF electrical current is typically delivered from a generator via connected electrodes that are placed in a patient's body, in a region of tissue that contains a neural structure suspected of transmitting pain signals to the brain. The electrodes generally include an insulated elongate member with an exposed conductive tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to a procedure whereby the ability of a neural structure to transmit signals is affected in some way and usually results in the complete inability of a neural structure to transmit signals, thus removing the pain sensations. This procedure may be done in a monopolar mode where a second dispersive electrode with a large surface area is placed on the surface of a patient's body to complete the circuit, or in a bipolar mode where a second radiofrequency electrode is placed at the treatment site. In a bipolar procedure, the current is preferentially concentrated between the two electrodes.

To extend the size of a lesion, radiofrequency treatment may be applied in conjunction with a cooling mechanism, whereby a cooling means is used to reduce the temperature of the electrode-tissue interface, allowing more energy or power to be applied without causing an unwanted increase in local tissue temperature that can result in tissue desiccation, charring, or steam formation. The application of more energy or power allows regions of tissue further away from the energy delivery device to reach a temperature at which a lesion can form, thus increasing the size/volume of the lesion.

The treatment of pain using high-frequency electrical current has been applied successfully to various regions of patients' bodies suspected of contributing to chronic pain sensations. For example, with respect to knee pain, which affects millions of individuals every year, high-frequency electrical treatment has been applied to several tissues, including, for example, the ligaments, muscles, tendons, and menisci. However, the existing cooled RF treatments of the knee and other regions of the body are confined to being performed in hospital-based settings due to the high cost of the probe assemblies and their associated radiofrequency generators, coolant fluid pumps, and other equipment.

Due to the large volume lesions generated by cooled radiofrequency ablation probe procedures, care must be taken when treating sensitive locations, particularly around areas that cannot sustain significant collateral ablative damage. Furthermore, existing cooled radiofrequency probes are often top-heavy and may impart a large torque about the probe insertion point due to the mass of the probe handle and the rigidity of the tubing and cable that are connected to the probe. As a result, the existing cooled RF probes are often unwieldy and difficult to manipulate, thereby increase the risk of improper insertion and tissue injury at the probe insertion site. Further, in existing treatments, each cooled radiofrequency probe must be attached to its own respective electrical and fluid supply, requiring the use of many cables and tubes in a small treatment area which may interfere with the surrounding probes.

Moreover, existing cooled radiofrequency probes are difficult to manufacture, requiring intense processes requiring long assembly cycle times including multiple long-duration curing stages. The manufacturing difficulty of the existing cooled RF probes thereby results in increased cost to manufacture. As a result of the increased cost of the probes, cooled RF treatments have been confined to hospital-based settings due to reimbursement constraints.

Consequently, there is a need for a system for treating chronic pain using cooled RF ablation techniques that is particularly optimized for treating a patient's knee, and more particularly improved cooled radiofrequency ablation probes that are particularly optimized for treating the tissue of a patient's knee joint and have a reduced manufacturing cost. Moreover, a cooled radiofrequency probe assembly that can be manufactured at a lower cost and thereby expand treatments into settings outside of hospitals, such as doctor's offices or ambulatory service centers, would be useful.

SUMMARY OF THE INVENTION

The present invention provides a cooled radiofrequency ablation probe assembly. The cooled radiofrequency probe assembly includes a first cooled radiofrequency ablation probe having an electrically and thermally-conductive energy delivery device, and a second cooled radiofrequency ablation probe having a second electrically and thermally-conductive energy delivery device; cooling fluid tubing for supplying the at least two cooled radiofrequency ablation probes with cooling fluid; and an electrical cable for supplying the first cooled radiofrequency ablation probe and the second cooled radiofrequency ablation probe with electrical energy. The first cooled radiofrequency ablation probe and the second cooled radiofrequency ablation probe are connected to the cooling fluid tubing in series.

In one particular embodiment, the first cooled radiofrequency ablation probe and the second cooled radiofrequency ablation probe can be tethered together by the cooling fluid tubing and/or the electrical cable.

In another embodiment, the cooling fluid tubing and the electrical cable can be each connected to the at least two probes at a respective probe handle.

In yet another embodiment, the cooling fluid tubing can include an inlet portion extending between an inlet connector and the first radiofrequency ablation probe.

In still another embodiment, the cooling fluid tubing can include a connecting tubing portion extending between the first cooled radiofrequency ablation probe and the second cooled radiofrequency ablation probe. Further, the connecting tubing portion can have a length sufficient to dissipate any heat captured by cooling fluid in the first radiofrequency ablation probe into the atmosphere prior to the cooling fluid entering the second radiofrequency ablation probe. Moreover, the connecting tubing portion can have a length in a range from about 60 cm to about 185 cm.

In one more embodiment, the cooling fluid tubing can include an outlet tubing portion extending between an outlet connector and the second radiofrequency ablation probe.

In an additional embodiment, the first cooled radiofrequency ablation probe and the second cooled radiofrequency ablation probe can be connected to the electrical cable in parallel.

In yet another embodiment, the electrical cable can connect the first cooled radiofrequency ablation probe and the second cooled radiofrequency ablation probe to a single electrical connector.

In still another embodiment, the electrical cable can be Y- or T-shaped.

In one more embodiment, the electrical cable can split at a grommet from a single electrical cable to a plurality of discrete electrical cables including at least a first split electrical cable and a second split electrical cable. Further, the first split electrical cable can connect to the first radiofrequency ablation probe and the second split electrical cable can connect to the second radiofrequency ablation probe. Moreover, a length of the single electrical cable can be shorter than a length of the cooling fluid tubing extending between the first cooled radiofrequency ablation probe and the second cooled radiofrequency ablation probe.

In yet another embodiment, the first radiofrequency ablation probe can include a first elongate member extending away from the cooling fluid tubing and the electrical cable, wherein the first electrically and thermally-conductive energy delivery device is located in the first elongate member, further wherein the second radiofrequency ablation probe can include a second elongate member extending away from the cooling fluid tubing and the electrical cable, wherein the second electrically and thermally-conductive energy delivery device is located in the second elongate member. Moreover, the first elongate member and the second elongate member can have unequal lengths. Further, the first elongate member can have a length in a range from about 30 to about 50 mm long, and the second elongate member can have a length in a range from about 50 to about 75 mm long. In another embodiment, the first elongate member and the second elongate member can have approximately equal lengths.

In still another embodiment, a length of the cooling tubing fluid, a length of the electrical cable, and a length of each of the first radiofrequency ablation probe and the second radiofrequency ablation probe are optimized to provide radiofrequency ablation treatment to a patient's knee.

In yet another embodiment, the cooling fluid tubing can be configured to provide the first radiofrequency ablation probe and the second radiofrequency ablation probe with cooling fluid from a single cooling fluid source.

In one more embodiment, the electrical cable can be configured to provide the first radiofrequency ablation probe and the second radiofrequency ablation probe with electrical energy from a single source.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
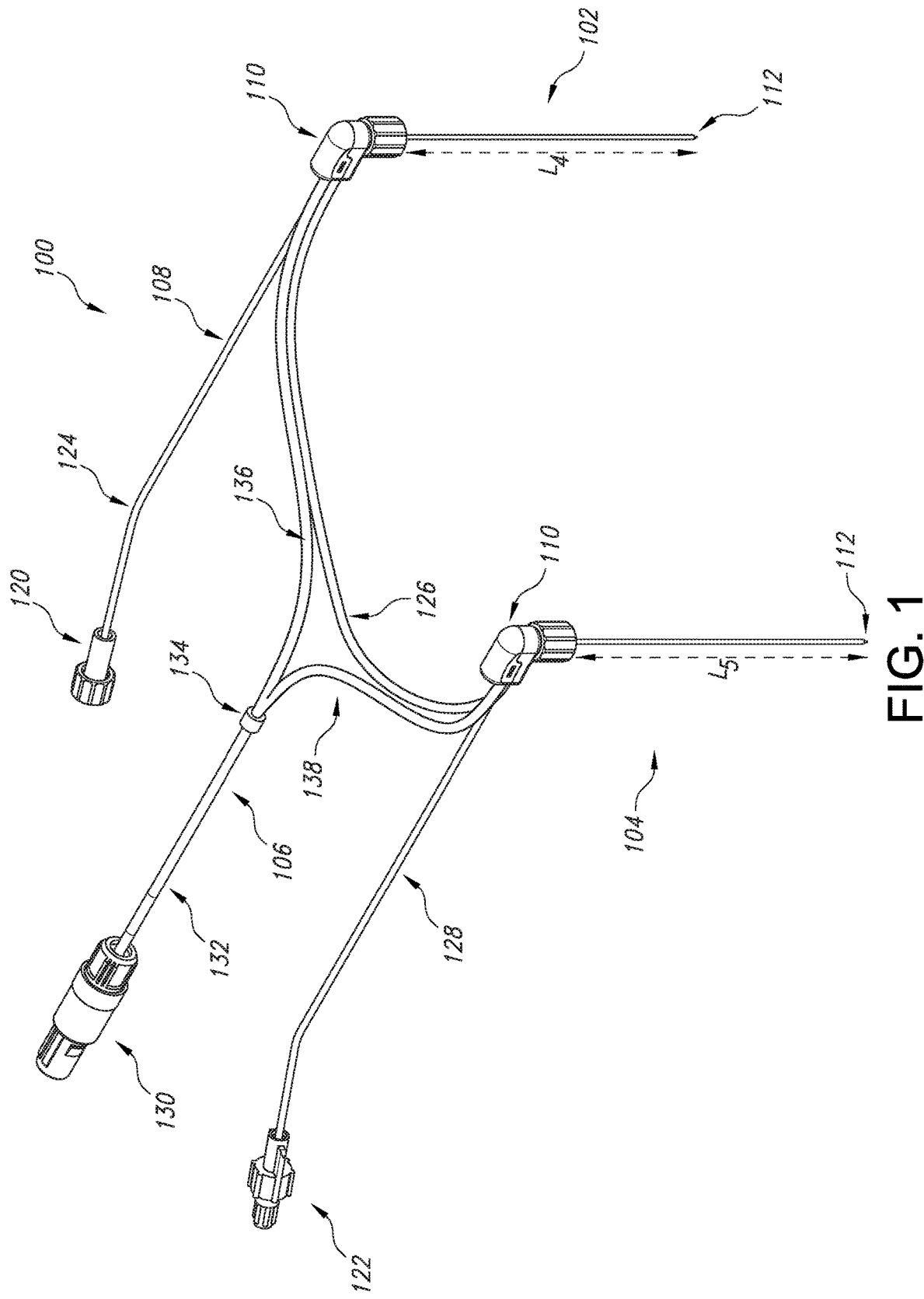
FIG. 1 illustrates a perspective view of a dual cooled radiofrequency probe assembly according to an embodiment of the present invention.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to the region of tissue that has been irreversibly damaged as a result of the application of thermal energy, and the invention is not intended to be limited in this regard. Furthermore, for the purposes of this description, proximal generally indicates that portion of a device or system next to or nearer to a handle of the probe (when the device is in use), while the term distal generally indicates a portion further away from the handle of the probe (when the device is in use).

Referring now to the drawings, FIG. 1 illustrates a cooled radiofrequency ablation probe assembly 100 of the present invention. As shown, the probe assembly 100 includes a first probe 102 and a second probe 104 which are arranged in series, with the second probe 104 being positioned downstream of the first probe 102. In an alternate embodiment, the probe assembly can include more than two probes. The probe assembly 100 further includes an electrical cable 106 for supplying energy to the probes 102 and 104, and cooling fluid tubing 108 for carrying cooling fluid to and from the probes 102 and 104. The electrical cable 106 and the cooling fluid tubing 108 communicate with each of the probes 102, 104 at a probe handle 110 of each probe.

Figure 2:
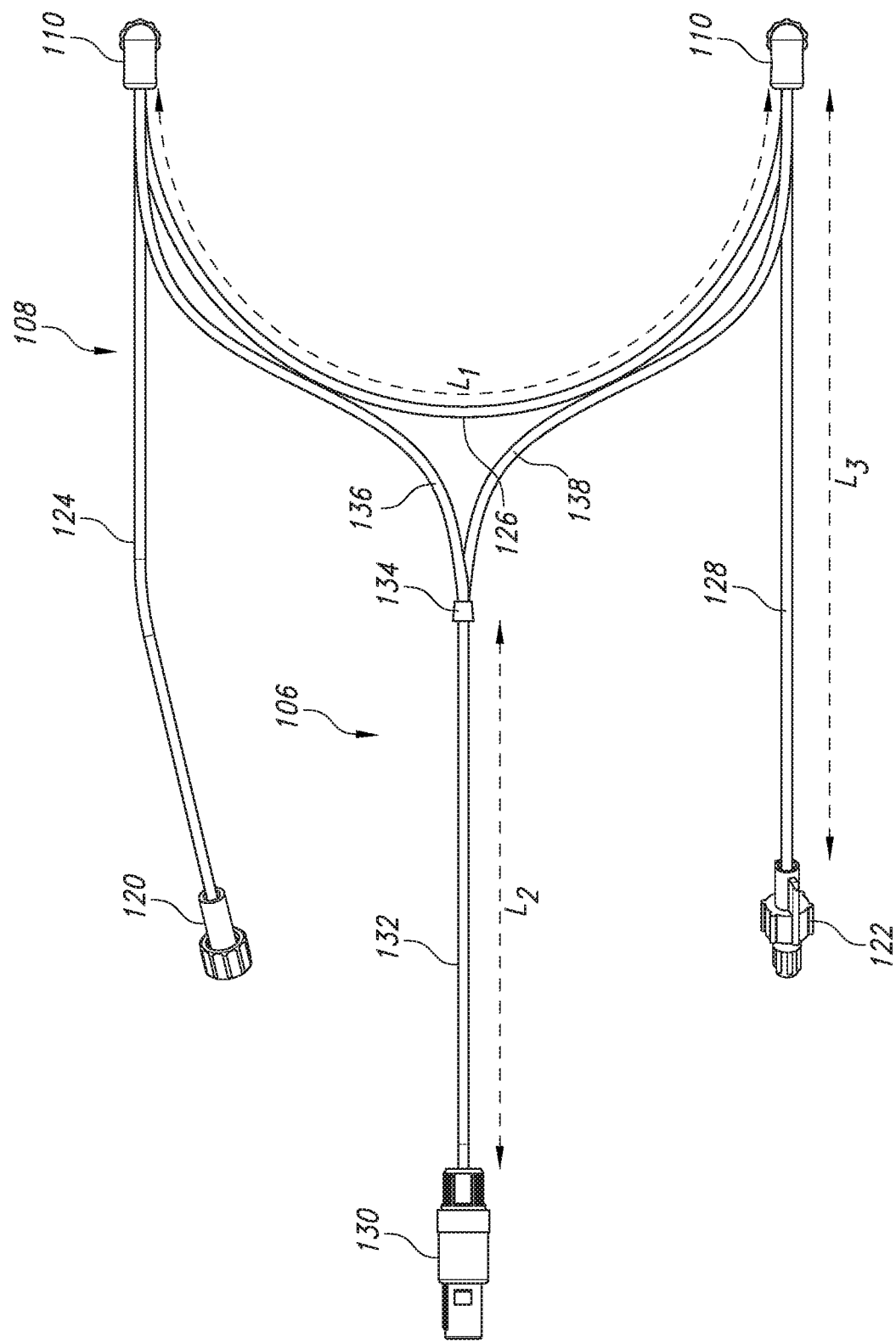
FIG. 2 illustrates a top view of the probe assembly of FIG. 1.

The electrical cable 106 may be formed as a Y-shaped electrical cable. Alternately, the electrical cable 106 may be T-shaped. The electrical cable 106 includes an electrical connector 130 located at an end of the cable 106 opposite from the probes 102, 104. The electrical connector 130 may be a 6-pin circular connector. The connector 130 is connected to a single electrical cable 132. The single electrical cable 132 splits at a grommet 134 into two discrete cables with three conductors each, forming a first probe electrical cable 136 which connects to the first probe 102 and a second probe electrical cable 138 which connects to the second probe 104. As shown in FIGS. 1-2, the probes 102, 104 can be connected to the electrical cable 106 in parallel via the first probe electrical cable 136 and the second probe electrical cable 138.

Still referring to FIGS. 1-2, the cooling fluid tubing 108 can include an inlet connector 120, for example a female Luer connector, for connecting to a cooling fluid source (not shown). The cooling fluid tubing 108 inlet portion 124 may extend from the inlet connector 120 to the first probe 102. A connecting tubing portion 126 of cooling fluid tubing 108 extends between the first probe 102 and the second probe 104, which is downstream of the first probe 102 along the fluid tubing 108. An outlet tubing portion 128 can extend from the second probe 104 to an outlet connector 122, for example a male Luer connector. In one embodiment, the outlet connector 122 may connect to the cooling fluid source (not shown) to form a closed-loop cooling fluid system. In an alternative embodiment, the outlet connector 122 may connect to a waste bag (not shown) for disposal of the cooling fluid.

The connecting tubing portion 126 can connect between the first probe 102 and the second probe 104 so that cooling fluid flows from the first probe 102 to the second probe 104 before flowing through outlet tubing portion 128 to the fluid source or waste bag (not shown). The connecting tubing portion 126 may cool the cooling fluid based on the temperature of ambient air. For example, if cooling fluid is heated as it flows through the first probe 102, the heat captured by the cooling fluid can be dissipated into the atmosphere by the ambient air temperature as the cooling fluid flows through connecting tubing portion 126 before reaching the second probe 104. The connecting tubing portion 126 can have a length sufficient to dissipate any heat captured by cooling fluid in the first probe into the atmosphere prior the cooling fluid flowing into the second probe 104.

The top view of the probe assembly 100 illustrated in FIG. 2 shows lengths of the electrical cable 106 and cooling fluid tubing 108 of the probe assembly 100. The length of the connecting tubing portion 126 and/or the first probe electrical cable 136 and second probe electrical cable 138 may dictate the farthest straight-line distance $L_1$ between the probes 102 and 104. The distance $L_1$ may be from about 24 inches (60 cm) to about 72 inches (185 cm), such as from about 36 inches (90 cm) to about 60 inches (155 cm). In one embodiment, the straight-line distance $L_1$ between probes 102 and 104 is about 48 inches (122 cm). The single electrical cable 132 extending from the grommet 134 to the electrical connector 130 has a length $L_2$ which may be from about 12 inches (30 cm) to about 36 inches (90 cm), such as from about 18 inches (45 cm) to about 30 inches (76 cm). In one embodiment, the length $L_2$ of the single electrical cable 132 may be about 24 inches (60 cm). The inlet tubing 124 and outlet tubing 128 may each have a length $L_3$ which may be from about 24 inches (60 cm) to about 72 inches (185 cm), such as from about 36 inches (90 cm) to about 60 inches (155 cm). In one embodiment, the distance $L_3$ of the inlet tubing 124 and outlet tubing 128 is about 48 inches (122 cm).

The length of the single electrical cable $L_2$, the distance $L_1$ between the probes, and the length $L_3$ of the tubing limits the cooled RF probe assembly 100 to be used for patient treatment sites that may be positioned close to a radiofrequency generation source and pump for the cooling fluid. For example, a patient's knee may be positioned on an outer edge of a bed, chair, or other surface and directly adjacent to the RF source and pump. In contrast, this embodiment may not be able to be used for treating a patient's spine because the relatively shorter lengths of the electrical cable 106 and the cooling fluid tubing 106 would not reach from the RF source and pump all the way to the center of a patient's back when the patient is laying face-down on a treatment bed or table.

Referring back to FIG. 1, extending from the handle 110 of each of the probes 102, 104 is an elongate member 112 forming a radiofrequency treatment assembly. In one embodiment, the first probe 102 may have a longer elongate member 112 than the elongate member 112 of the second probe 104. For example, the first probe 102 may have an elongate member length $L_4$ of about 50 mm (1.97 inches) or about 75 mm (2.95 inches), and the second probe 104 may have an elongate member length $L_5$ of about 30 mm (1.18 inches) or about 50 mm (1.97 inches). In another embodiment, the first probe 102 and the second probe 102 may have equal elongate member lengths of about 30 mm (1.18 inches) or about 50 mm (1.97 inches). In yet another embodiment, the elongate member 112 of the first probe 102 may be shorter than the elongate member 112 of the second probe 104.

Figure 3:
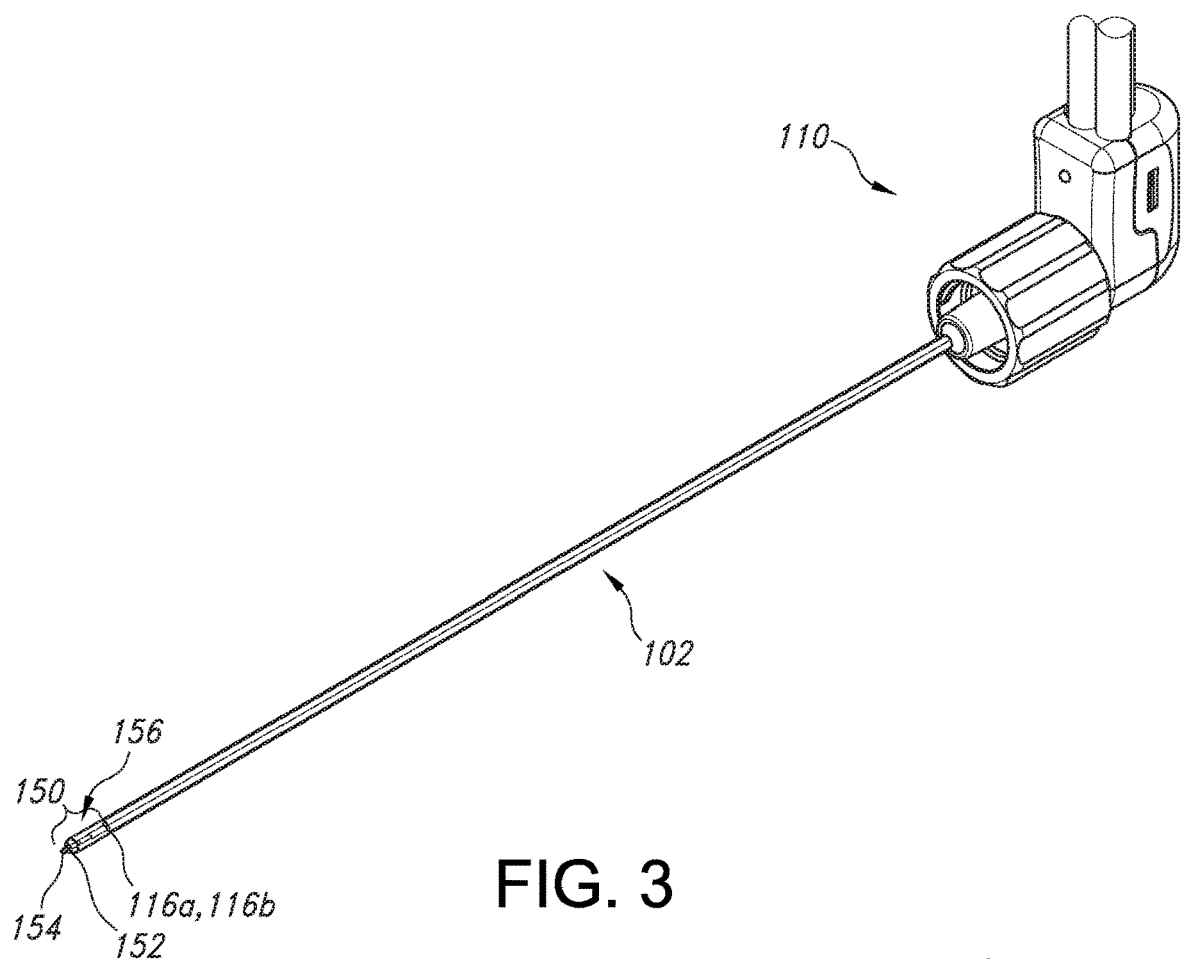
FIG. 3 illustrates a perspective view of a radiofrequency treatment assembly of the probe assembly of FIG. 1.
Figure 4:
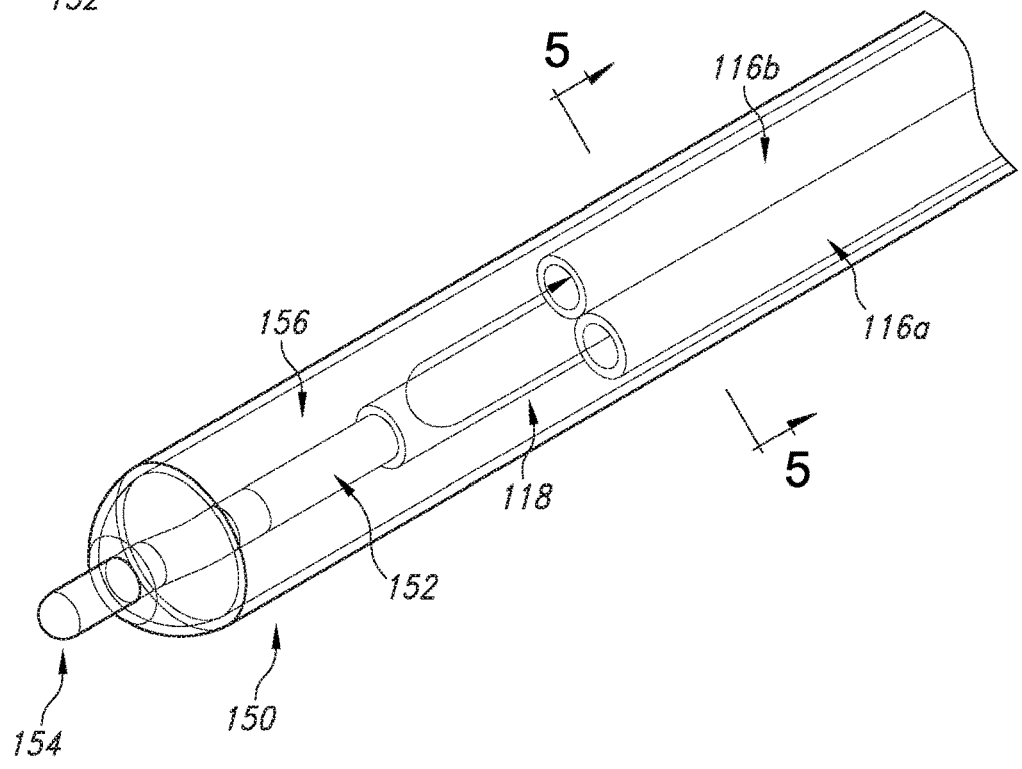
FIG. 4 illustrates a cut-away view of a distal end of the radiofrequency treatment assembly shown in FIG. 3.
Figure 5:
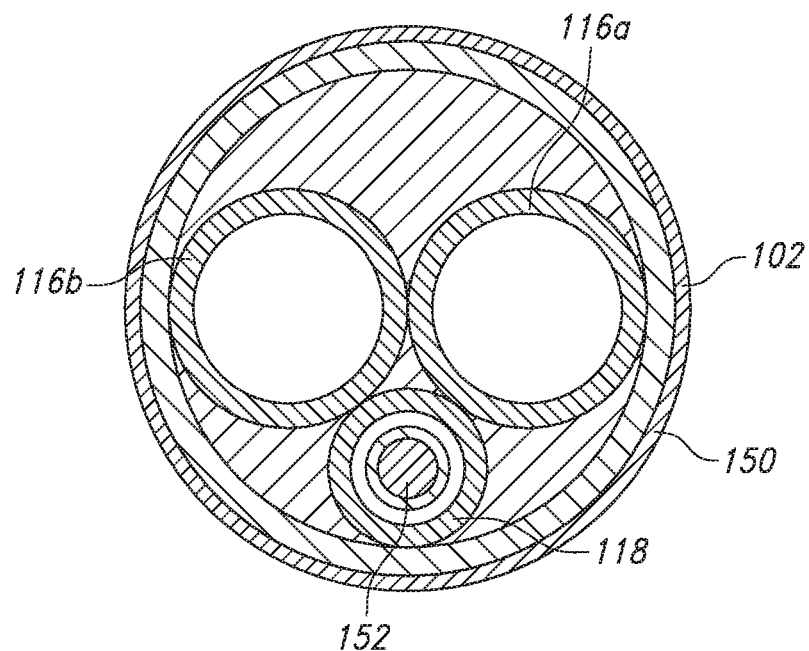
FIG. 5 illustrates a cross-sectional view of the distal end of the radiofrequency treatment assembly of FIG. 4.

Referring now to FIGS. 3 and 4, the elongate member 112 of each probe 102, 104 forms an electrocap assembly that is thermally and electrically conductive for delivering electrical or radiofrequency energy to the patient's tissue. A distal end 150 of the elongate member 112 opposite the probe handle 110 forms an active tip 154 for delivering the cooled radiofrequency treatment to the patient's tissue. The electrocap assembly may include at least one fluid conduit 116 within the elongate member 112, such as an inlet fluid conduit 116a and an outlet fluid conduit 116b, for delivering cooling fluid to and from the active tip 154. The electrocap assembly may additionally include a thermocouple hypotube 118 extending the length of the elongated member 112 and protruding from the distal end of the elongated member. The thermocouple hypotube 118 may include a wire 152 made from an electrically conductive material such as constantan. The wire 152 can be insulated along the entire length of the elongated member 112 and welded to the hypotube 118 at a distal end 150 of the electrocap assembly to form a thermocouple 154. The cooling fluid may be circulated in a volume 156 within the distal end 150 of the electrocap assembly adjacent the thermocouple 154 to control the temperature of the active tip 114. FIG. 5 illustrates a cross-sectional view of the distal end 150 of the elongated member 112.

Figure 6:
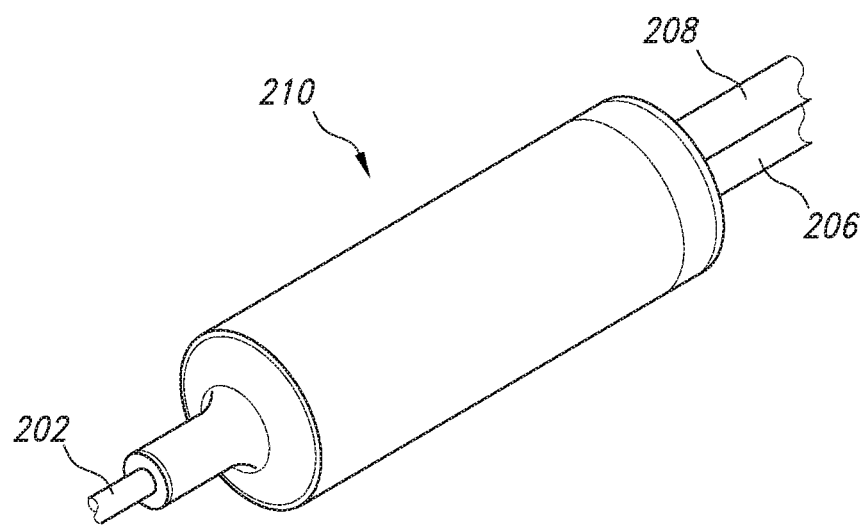
FIG. 6 illustrates a perspective view of another embodiment of a probe handle of the dual cooled radiofrequency probe assembly of the present invention.

As shown in FIG. 6, in an alternative embodiment, the assembly 100 may include an alternative probe handle 210 for the dual cooled radiofrequency probe assembly. The probe handle 210 can be generally cylindrical shaped and can communicate with an electrical cable 204 and cooling fluid tubing 208 at one end and an elongated radiofrequency treatment probe 202 at an opposite end. The cylindrical shape of the probe handle 210 extends in a longitudinal direction that is in parallel with the electrical cable 204, cooling fluid tubing 208, and elongated radiofrequency treatment probe 202, as shown in FIG. 6.

Turning back to FIG. 1, probes 102 and 104 having unequal elongate member lengths are shown. Providing probes 102 and 104 with staggered probe elongate member lengths $L_4$ and $L_5$, for example about 50 mm and about 30 mm, respectively, further conforms the treatment to the knee anatomy by enabling one deeper and one more superficial treatment simultaneously at different sites within one knee joint. Additionally, the relatively short (less than about 75 mm, and in some embodiments less than or equal to about 50 mm) elongate member lengths $L_4$ and $L_5$ of the probes 102 and 104 can be optimized for treatment of the knee because treatment sites in the knee joint are superficially located just under the skin. In comparison, cooled RF probes for treatment of the spine or hip may require have longer elongate member lengths to penetrate deep into the patient's tissue to reach the target nerves. Furthermore, having shorter elongate member lengths of the probes reduces the length of the probes extending outside the patient's tissue, which thereby can increase the stability of the placement of the cooled RF probes. When the length of the probe extending outside the patient's tissue is reduced, the moment arm of the probe and thereby possible torque applied to the treatment site by rotation or instability of the probes decreases.

In yet another embodiment, non-cooled radiofrequency ablation probes may be tethered for treatment of the knee. Such an embodiment can include an identical system as the cooled RF probe assembly 100 but does not include the cooling fluid tubing 108. This embodiment can include a Y- or T-shaped electrical cable 106 for connecting two radiofrequency ablation probes to a single electrical source through a circular connector 130.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A cooled radiofrequency ablation probe assembly comprising:
    a first cooled radiofrequency ablation probe comprising a first electrically and thermally-conductive energy delivery device, and a second cooled radiofrequency ablation probe comprising a second electrically and thermally-conductive energy delivery device;
    cooling fluid tubing for supplying the first cooled radiofrequency ablation probe and the second cooled radiofrequency ablation probe with cooling fluid, the cooling fluid tubing comprising a connecting tubing portion extending between the first cooled radiofrequency ablation probe and the second cooled radiofrequency ablation probe such that the first cooled radio frequency ablation probe and the second cooled radiofrequency ablation probe are spaced apart by the connecting tubing portion, the connecting tubing portion ranging from 60 cm to 185 cm in length to allow heat captured by the cooling fluid in the first radiofrequency ablation probe to dissipate into the atmosphere prior to the cooling fluid entering the second radiofrequency ablation probe; and
    an electrical cable for supplying the first cooled radiofrequency ablation probe and the second cooled radiofrequency ablation probe with electrical energy, the electrical cable splitting to a plurality of discrete electrical cables comprising a first split electrical cable connects to the first cooled radiofrequency ablation probe and a second split electrical cable connects to the second cooled radiofrequency probe, wherein the first cooled radiofrequency ablation probe and the second cooled radiofrequency ablation probe are connected to the cooling fluid tubing in series.

2. The probe assembly of claim 1, wherein the first cooled radiofrequency ablation probe and the second cooled radiofrequency ablation probe are tethered together by the cooling fluid tubing and/or the electrical cable.

3. The probe assembly of claim 1, wherein the cooling fluid tubing and the electrical cable are each connected to the first cooled radiofrequency ablation probe and the second cooled radiofrequency ablation probe at a respective probe handle.

4. The probe assembly of claim 1, wherein the cooling fluid tubing comprises an inlet portion extending between an inlet connector and the first cooled radiofrequency ablation probe.

5. The probe assembly of claim 1, wherein the cooling fluid tubing comprises an outlet tubing portion extending between an outlet connector and the second cooled radiofrequency ablation probe.

6. The probe assembly of claim 1, wherein the first cooled radiofrequency ablation probe and the second cooled radiofrequency ablation probe are connected to the electrical cable in parallel.

7. The probe assembly of claim 1, wherein the electrical cable connects the first cooled radiofrequency ablation probe and the second cooled radiofrequency ablation probe to a single electrical connector.

8. The probe assembly of claim 1, wherein the electrical cable is Y- or T-shaped.

9. The probe assembly of claim 1, wherein the electrical cable splits at a grommet from a single electrical cable to the plurality of discrete electrical cables including at least the first split electrical cable and the second split electrical cable.

10. The probe assembly of claim 9, wherein a length of the electrical cable is shorter than the length of the cooling fluid tubing extending between the first cooled radiofrequency ablation probe and the second cooled radiofrequency ablation probe.

11. The probe assembly of claim 1, wherein the first cooled radiofrequency ablation probe includes a first elongate member extending away from the cooling fluid tubing and the electrical cable, wherein the first electrically and thermally-conductive energy delivery device is located in the first elongate member, further wherein the second cooled radiofrequency ablation probe includes a second elongate member extending away from the cooling fluid tubing and the electrical cable, wherein the second electrically and thermally-conductive energy delivery device is located in the second elongate member.

12. The probe assembly of claim 11, wherein the first elongate member and the second elongate member have unequal lengths.

13. The probe assembly of claim 12, wherein the first elongate member has a length in a range from about 30 to about 50 mm long, and the second elongate member has a length in a range from about 50 to about 75 mm long.

14. The probe assembly of claim 11, wherein the first elongate member and the second elongate member have approximately equal lengths.

15. The probe assembly of claim 1, wherein the length of the cooling tubing fluid, a length of the electrical cable, and a length of each of the first cooled radiofrequency ablation probe and the second cooled radiofrequency ablation probe are optimized to provide radiofrequency ablation treatment to a patient's knee.

16. The probe assembly of claim 1, wherein the cooling fluid tubing is configured to provide the first cooled radiofrequency ablation probe and the second cooled radiofrequency ablation probe with the cooling fluid from a single cooling fluid source.

17. The probe assembly of claim 1, wherein the electrical cable is configured to provide the first cooled radiofrequency ablation probe and the second cooled radiofrequency ablation probe with electrical energy from a single source.

18. The probe assembly of claim 1, wherein the first split electrical cable and the second split electrical cable split from the electrical cable at a location proximate a midpoint of the connecting tubing portion of the cooling fluid tubing.

19. The probe assembly of claim 1, wherein a length of the first split electrical cable and a length of the second split electrical cable is less than a length of the connecting tubing portion of the cooling fluid tubing.

* * * * *